US007722897B2

(12) United States Patent
Dupont et al.

(10) Patent No.: US 7,722,897 B2
(45) Date of Patent: *May 25, 2010

(54) PATCH FOR SCREENING AND SENSITIZATION STATE OF A SUBJECT WITH RESPECT TO AN ALLERGEN AND USE THEREOF

(75) Inventors: Christophe Dupont, Clamart (FR); Bertrand Dupont, Aix En Provence (FR); Pierre-Yves Vannerom, Paris (FR); Stephane Benhamou, Saint Barthelemy (FR); Pierre-Henri Benhamou, Paris (FR)

(73) Assignee: DBV Technologies, Boulogne (FR)

( * ) Notice: Subject to any disclaimer, the term of this patent is extended or adjusted under 35 U.S.C. 154(b) by 1578 days.

This patent is subject to a terminal disclaimer.

(21) Appl. No.: 10/659,566

(22) Filed: Sep. 10, 2003

(65) Prior Publication Data

US 2004/0047902 A1    Mar. 11, 2004

Related U.S. Application Data

(63) Continuation of application No. PCT/FR02/00804, filed on Mar. 6, 2002.

(30) Foreign Application Priority Data

Mar. 31, 2001  (FR) .................................. 01 03382

(51) Int. Cl.
*A61L 15/16*  (2006.01)
*A61N 1/30*  (2006.01)

(52) U.S. Cl. ........................................ 424/448; 640/20
(58) Field of Classification Search .................. 424/448
See application file for complete search history.

(56) References Cited

U.S. PATENT DOCUMENTS

| | | | | | |
|---|---|---|---|---|---|
| 3,645,852 | A | * | 2/1972 | Axen et al. | 435/181 |
| 3,837,340 | A | * | 9/1974 | Counter | 604/307 |
| 3,894,531 | A | | 7/1975 | Saunders, Jr. | 128/2 W |
| 4,435,180 | A | | 3/1984 | Leeper | |
| 4,450,844 | A | | 5/1984 | Quisno | 128/743 |
| 4,743,249 | A | | 5/1988 | Loveland | |
| 4,788,971 | A | * | 12/1988 | Quisno | 600/556 |
| 4,821,733 | A | * | 4/1989 | Peck | 600/361 |
| 4,836,217 | A | * | 6/1989 | Fischer | 600/556 |
| 5,236,455 | A | | 8/1993 | Wilk et al. | |
| 5,438,984 | A | * | 8/1995 | Schoendorfer | 600/573 |
| 5,827,608 | A | | 10/1998 | Rinehart et al. | |
| 6,093,419 | A | | 7/2000 | Rolf | |
| 6,142,954 | A | | 11/2000 | Anhauser et al. | |
| 6,210,705 | B1 | * | 4/2001 | Mantelle et al. | 424/448 |
| 2002/0102291 | A1 | * | 8/2002 | Mantelle et al. | 424/448 |
| 2002/0151487 | A1 | * | 10/2002 | Nickoloff et al. | 514/12 |
| 2002/0168761 | A1 | * | 11/2002 | Gour et al. | 435/325 |
| 2003/0064088 | A1 | * | 4/2003 | Carvalho et al. | 424/423 |
| 2004/0047902 | A1 | * | 3/2004 | Dupont et al. | 424/449 |
| 2004/0137004 | A1 | | 7/2004 | Glenn et al. | |
| 2006/0002949 | A1 | | 1/2006 | Glenn et al. | |
| 2006/0147509 | A1 | | 7/2006 | Kirkby et al. | |
| 2007/0048361 | A1 | | 3/2007 | Dupont et al. | |

FOREIGN PATENT DOCUMENTS

| | | |
|---|---|---|
| EP | 0 107 832 A2 | 10/1983 |
| EP | 0409465 A1 | 1/1991 |
| EP | 0976396 A1 | 2/2000 |
| EP | 1031346 A1 | 8/2000 |
| FR | 2527450 A | 12/1983 |
| GB | 501873 A | 3/1939 |
| GB | 1013895 A | 12/1965 |
| JP | 06238008 | 8/1994 |
| JP | 2000-083580 | 12/1999 |
| WO | WO 96/32142 | 10/1996 |
| WO | WO9825521 | 6/1998 |
| WO | WO 98/31315 A1 | 7/1998 |
| WO | WO 00/43058 A1 | 7/2000 |
| WO | WO 02/30281 A1 | 4/2002 |
| WO | WO 02/074325 A1 | 9/2002 |
| WO | WO 02/089717 A1 | 11/2002 |
| WO | WO 02/093998 A2 | 11/2002 |
| WO | WO 2004/030696 A2 | 4/2004 |
| WO | WO 2004/052425 A2 | 6/2004 |

OTHER PUBLICATIONS

Fentanyl Patch, Brand Name: Duragesic Patches, (2007), pp. 1-6.*
Polypropylene, [online] retrieved Jan. 5, 2008 92008), retrieved from http:pslc.ws/mactest/pp.htm, printed pp. 1-3.*

(Continued)

*Primary Examiner*—Sreeni Padmanabhan
*Assistant Examiner*—Timothy E Betton
(74) *Attorney, Agent, or Firm*—Jones Day; Nicola A. Pisano

(57) ABSTRACT

A patch comprises a support having electrostatic properties. The periphery of the support is coated with an adhesive material, and all or part of the non-adhesive surface of the support is directly covered with at least one biologically active substance in the form of particles. The particles remain in contact with the non-adhesive part of the support as a result of the electrostatic forces.

24 Claims, 1 Drawing Sheet

OTHER PUBLICATIONS

Antelman (WO/2001/049302), (2000).*
Lipper et al. (WO 02/076379) (2000).*
Advisory Action mailed Apr. 29, 2009, U.S. Appl. No. 11/411,531.
Office Action mailed Apr. 16, 2008, U.S. Appl. No. 11/411,531.
Office Action mailed Feb. 11, 2009, U.S. Appl. No. 11/411,531.

* cited by examiner

PATCH FOR SCREENING AND SENSITIZATION STATE OF A SUBJECT WITH RESPECT TO AN ALLERGEN AND USE THEREOF

CROSS REFERENCE TO RELATED APPLICATIONS

This application is a continuation of International Application PCT/FR 02/00804 filed Mar. 6, 2002 and published, in French, on Sept. 19, 2002 as publication WO 02/071950, and claims priority from Application No. 01.03382 filed Mar. 31, 2001 in France.

The invention relates to a novel form of patch able to deliver a biologically active substance to the epidermis. It is in particular related to a patch intended in particular for screening the sensitization state of a subject with respect to an allergen. It also relates to the use of said patch, in particular for screening the sensitization state of a subject with respect to an allergen.

In the remainder of the description, the term "biologically active substance" denotes a substance for diagnostic, therapeutic, cosmetic or preventive (for example a vaccine) purposes, which is in the form of individualized or agglomerated particles.

The invention will be more particularly described in relation to the allergens, considered, within the meaning of the preceding definition, as substances for diagnostic purposes, i.e. substances for screening the sensitization state of a subject with respect to a given allergen.

In the remainder of the description, the expression "contact allergen" will denote any allergen capable of causing a reaction on direct contact with the skin, without any reaction at distance, when said allergen is brought into contact with a subject's body. This type of allergen is found in a certain number of natural or synthetic products which, when they are brought into contact with the skin of a subject, bring about a "contact" allergy which causes a local skin reaction characterized by various phenomena, such as rash, itching, the appearance of vesicles and eczema. Such allergens are entirely known to those skilled in the art and are precisely listed in the literature, in particular in document U.S. Pat. No. 4,836,217. Many contact allergies are known, and in particular allergies to metals, such as, for example, the nickel contained in watch straps or the chromium contained in cement, but also allergies to fragrances and to lanolin contained in cosmetic products, allergies to active substances, such as neomycin, flavin contained in certain medicinal products, etc.

The present invention relates not only to contact allergies, but also and especially to all the allergic manifestations which may manifest themselves not exclusively by a skin reaction on contact with the allergen, but also by a certain number of symptoms lying at a distance from the site of contact with the allergen, for example anaphylactic shock, diarrhea, sinusitis, asthma, generalized eczema, urticaria, etc. This is true for allergies to acarids, pollens, animal hairs, diverse foods and various substances of plant or animal origin. Many allergens are implicated, thus, for example, acarids, pollens, animal hairs or feathers, etc., which are sometimes referred to as "respiratory" allergens, are the cause of respiratory manifestations of the rhinitis or asthma type. Similarly, groundnut, egg, milk and wheat, which are sometimes referred to as "food" allergens, are the cause of digestive pathologies, such as chronic diarrhea in children, or of anaphylactic pathologies, such as anaphylactic shock, in response, for example, to ingesting groundnut. Allergy to latex is also entirely known and leads to symptoms of the anaphylactic type, causing the patient to run a potentially serious peroperative risk. The majority of these allergens are precisely listed in document EP-A-107832.

The means for diagnosing allergy are based on a battery of tests, at the forefront of which are skin tests. The appearance of skin reactivity on contact with the allergen results in a local inflammatory skin reaction, which is either moderate in the form of erythema (first clinical element of the inflammatory reaction), or in the form of a papula also indicating the presence of local edema (other component of the inflammatory reaction). The skin reactivity of an allergen other than a contact allergen is explained by the constant circulation of immunological elements in the blood, allowing lymphocytes sensitized by the allergens, which have entered the body via the respiratory or digestive tracts, to also lie within the skin.

Several skin tests are today provided for detecting the sensitization state of an individual with respect to both contact allergens and respiratory and food allergens.

Among these, the test referred to as "Prick Test" is in particular known, which test concerns all allergens capable of triggering an immediate skin reaction to food or respiratory allergens. During this test, a solution containing the allergen is deposited onto the skin, and then said allergen is brought into contact with the immunological elements by means of a stylet which perforates the superficial part of the dermis through the solution. The Prick Test is read after half an hour of the dermis being in contact with the allergen. In other words, and as already mentioned, this test makes it possible to detect an immediate reaction, which is in general IgE-dependent, i.e. using a type-E immunoglobulin reactivity. The reading is performed by comparison with a positive control, such as histamine, and a negative control, physiological saline or solvent used to dilute the allergens. The drawback of the Prick Test lies, firstly, in the fact that it is painful in nature due to the perforation of the dermis with the stylet or the needle and, secondly, and especially, in the fact that it explores exclusively an immediate reactivity.

Now, it appears that a certain number of allergic reactions occur in a delayed or semi-delayed manner, within a period of several hours to several days. It has, moreover, been noted that simple contact of the skin with an allergen caused the appearance of systemic reactions. It is therefore deduced therefrom that the allergen diffuses through the skin in such a way that it can trigger immediate reactions just as it can trigger delayed reactions.

Based on this observation, it has proposed to deposit the allergens on supports intended to be maintained in long-lasting contact with the skin, so as to allow the allergen to pass through the skin and thus to trigger a skin reaction. Two main types of test have been developed and are known under the generic term "patch test".

A first patch is known under the name FINN CHAMBERS®. It comprises an adhesive support to which are bonded small metal cupules approximately one centimeter in diameter. These cupules, 2 to 3 millimeters in depth, receive diluted allergens deposited onto a cellulose support not dependent on the cupule, the mixture being prepared extemporaneously from the native product or from allergens in suspension. The cellulose support is placed at the bottom of the cupule and the cupule is then attached to the patient's skin. The test is read after 48 hours, after removing the material, cleaning the skin and waiting for a short period of time, approximately half an hour, to allow specific local phenomena, associated with the pressure of the edge of the cupule on the skin or with the presence of the adhesive, to disappear. The positive reaction combines erythema, edema and a macular rash at the point of contact. It is compared with that caused by a negative control (cellulose support simply dampened with water). The interpretation is generally easy, but the reaction is not however, precisely quantifiable. FINN CHAMBERS® are used to test all the categories of allergens, whether contact allergens or others. In particular, the allergen/cellulose mixture prepared extemporaneously can, for example, contain foods in order to search for a food allergy, pollen in order to search for a respiratory allergy, or a dye or a metal in order to search for a contact allergy.

While this method makes it possible to use allergens of infinite variety, it has the drawback, however, of being difficult to use. Specifically, a certain number of errors can appear due to the fact, for example:

- that the cellulose support is moved while it is put in place;
- that the allergenic mixture, in too great an amount, contaminates the neighboring cavities;
- that the concentration of the allergen is too low to cause an allergic reaction;
- that the amount of allergen used is variable and does not allow the test to be standardized.

Moreover, if the test is used to detect several allergens, there is a risk of confusion during the interpretation, due to the fact that the allergens used cannot be pinpointed on the adhesive supports. In addition and especially, this type of test requires having allergens which are fresh or in suspension, and which must be solubilized or dispersed in a solvent extemporaneously, i.e. before the test is applied to the skin.

In conclusion, all of the manipulations required make this test random and limit it to specialized centers having trained personnel. As a result, the use of this type of test routinely is particularly limited, in particular in doctors' surgeries.

A patch known under the name LEUKOTEST® is prepared according to a principle similar to the FINN CHAMBERS® described above, with the difference that the PVC chambers are included in the adhesive support and not bonded to the adhesive support, and contain cellulose which is not removable, but remains attached to the cupule.

As above, the test is prepared extemporaneously with ready-to-use allergens which are fresh or in suspension. It is easier to use than the FINN CHAMBERS®, but it comprises, however, many handling error risks. The following are thus noted:

- the lack of control of the amount of allergen introduced into each chamber;
- the lack of indication concerning the nature of the allergens used on the plastic supports;
- and also the need to have the allergens in a form which is suitable for being deposited on the cellulose support.

A second type of patch is known under the name TRUE TEST® and is described more precisely in document U.S. Pat. No. 4,836,217. The TRUE TEST® deliminates the presence of the metal cupules, which it substitutes with a gel, into which the allergens are incorporated, the gel being applied directly on an adhesive strip. The allergens, only involving exclusively contact allergens, can be incorporated into the gel in various forms. Thus, if the allergen is soluble in the solvent contained in the gel, then the allergen is directly incorporated into the gel. On the other hand, if the allergen is insoluble, it is necessary to disperse it as homogeneously as possible directly in the gel. The main drawback of this type of patch is that it requires a cellulose support or a gel, capable of interacting with the allergen, and that it provides no guarantee of maintaining allergens of organic origin in their reactogenic state of origin.

More particularly applied to the case of the allergens, the first problem which the invention proposes to solve is to provide a patch which makes it possible to test all allergens and, in addition, to guarantee that organic allergens are maintained in their reactogenic state.

A second problem which the invention proposes to solve is to develop a ready-to-use patch, i.e. a patch which requires no extemporaneous preparation of the allergen.

A third problem which the invention proposes to solve is to provide a patch capable of containing and of delivering, on contact with the skin, a given amount of allergen which is constant from one patch to another, this particularity ensuring that the test is reliable and reproducible.

To do this, the invention provides a patch which is characterized in that it is in the form of a support having electrostatic properties, the periphery of which is coated with an adhesive material, all or part of the non-adhesive surface of the support being directly covered with at least one biologically active substance in the form of particles, said particles being kept in contact with the non-adhesive surface of the support as a result of electrostatic forces.

In a preferred embodiment, the biologically active substance is in the form of an allergen.

The patch of the invention therefore makes it possible to use the allergens in the form of particles in the pure state or after transformation, thus making it possible to involve all allergens, whatever the consistency and the form of the allergen in the fresh state. Moreover, the use of allergens in pure, native, whole or fractionated form, i.e. in their reactogenic state of origin, and without any addition of gel, of solvent or of support, makes it possible not only to have a patch which does not alter the conservation of the allergen, but also a patch which is ready-to-use, besides the preparation of the skin prior to its application.

Moreover, and in an advantageous embodiment, the support has an allergen marking device thus enabling the user to avoid any error during application to the skin or removal of the patch. The marking device can be in the form of marking printed on the back of the support, of a temporary tattoo left at the surface of the skin when the patch is removed, or else of a self-adhesive disk maintained on the adhesive part of the support and separated therefrom when the patch is removed.

As regards the form of the allergen in the fresh state, three hypotheses are possible. In a first hypothesis, the natural allergen is in the form of a powder, i.e. already in the form of individualized particles, such that it is not necessarily required to transform it (for example wheat flour), other than perhaps decreasing the size of the particles thereof.

In a second hypothesis, the allergen is in a more or less large solid form. In this case, it is necessary to reduce it to individualized particles, optionally after transformation aimed at ensuring its conservation without denaturation. This is the case, for example, of peanuts in the case of a food allergy to groundnut.

In a third hypothesis, the natural allergen is in liquid form. This is the case, for example, of milk, also implicated in some food allergies, which must, in this case, be lyophilized so as obtain a powdered form. In certain cases, it will be necessary to use only one of the purified fractions of the test allergen. This is the case, for example, of the protein fraction of egg, of albumin, or of cow's milk, or even of the proteins only of lactoserum extracted from cow's milk.

In the case of liquid allergens, the powdered form can be obtained by known techniques such as, for example, lyophilization (freezing and sublimation under vacuum) or heating and spraying, the choice of these techniques, in particular the degree of micronization, being left to the assessment of those skilled in the art as a function of the physicochemical characteristics of the allergen under consideration.

To ensure conservation of the patch in its packaging, and in particular to avoid modification of the allergen by ambient air, the particles undergo a particular treatment, such as lyophilization, pasteurization or ionization, and more particularly any treatment known to those skilled in the art. Whatever the biologically active substance that it contains, the patch is also prepared and/or conserved under vacuum and has, opposite the support, a label which can be peeled off and which is intended to be removed before the patch is applied to the skin.

According to an essential characteristic of the invention, the patch of the invention comprises a support having electrostatic properties.

In the remainder of the description and in the claims, the expression "electrostatic support" denotes any support made of a material capable of accumulating electrostatic charges and of conserving them by thus developing maintaining forces, in particular by rubbing, heating or ionization, or any other technique known to those skilled in the art. The charges which appear on one side or the other of the surface of the support can be positive or negative depending on the material constituting said support and on the means used to make them appear. In all cases, the positive or negative charges distributed over the surface of the support cause forces of attraction on conducting or non-conducting materials; in the case in point, on the allergen in the form of individualized or agglomerated particles. It may also so happen that it is said particles which are ionized, which can then cause the same type of electrostatic forces of attraction between these particles and the support. Thus, one of the advantages of the patch of the invention is that it allows precise metering of the surface mass of the allergen, or more generally of the biologically active substance, which is deposited and which is constant from one batch to another, as a function:

firstly, of the choice of the support and of its ability to store electrical charges on its surface;

of the type of particles of allergen;

and, secondly, of the flow of particles during the phase of depositing the allergen on the non-adhesive surface of the support.

In practice, any material can be used as support provided that the required electrostatic qualities. In particular, the support consists of glass or of a polymer chosen from the group comprising cellulose plastics (CA, CP), polyvinyl chlorides (PVCs), polypropylenes, polystyrenes, polycarbonates, polyacrylics, in particular poly(methyl methacrylate) (PMMA), fluoropolymers (PTFE for example), etc. This list is in no way limiting. Glass will advantageously be chosen if a particularly hypoallergenic support is desired.

Consequently, the support may be rigid or flexible, may or may not be hydrophilic, and may or may not be translucent, depending on the constituent material. In the case of glass, the support can then made unbreakable by bonding a sheet of plastic to the glass.

In an advantageous embodiment, a transparent support is chosen, which makes it possible, where appropriate, to directly observe the appearance of a reaction, without necessarily having to remove the patch.

In order to even further refine the detection of the inflammatory reaction, the patch has, on the adhesive surface or on the non-adhesive surface, a device sensitive to the physicochemical reactions of the skin noted during the local inflammatory reaction induced by a positive reaction. It may be a colored indicator sensitive to local variations in pH, for example. In this case, it is possible to envisage a reading system facilitating interpretation, independent of the local reaction.

In order to reactivate the electrostatic forces at the surface of the support and thus to reinforce the bonds of the biologically active substance, in particular of the allergen, with the support just before application, the back of the support is covered with a label which can be peeled off, to be removed during the application, which also makes it possible to conserve the allergens in the dark.

The transport of the allergenic molecules thus stored in the patch is ensured by the sweat secreted by the skin within the area delimited by the patch and which becomes loaded with allergenic molecules on contact therewith. The effectiveness of the patch and therefore its sensitivity is therefore greatly conditioned by the creation of a liquid phase, in which the allergen is in solution or in suspension, thus promoting its passage through the pores. Consequently, the patch must have characteristics making it possible to solve the following two problems:

- preventing evaporation of the sweat,
- and allowing circulation of the sweat.

As regards the problem of evaporation of the sweat, this is obtained, firstly, by virtue of the impermeability of the support and, secondly, by virtue of the peripheral adhesive area which makes an airtight joint and delimits a hermetically closed space between the skin and the support.

To solve the problem of circulation of the sweat, the support advantageously has, in the region not coated with adhesive material, a depression forming a hollow. This depression is obtained by formatting under hot or under cold conditions, and makes it possible to deposit the allergen in the hollow, such that said allergen is not pressing against the skin and does not alter the blood circulation in the area under consideration. This depression also makes it possible not to bring the allergen into contact with the layer which can be peeled off, which is removed before the patch is applied to the skin. Advantageously, the area defined by the hollow is maintained under vacuum.

In other words, the allergen, maintained in an original and reversible manner on the support by electrostatic forces, is entirely released into the cavity thus obtained and mixes with the sweat, which is more readily secreted due to the increase in local heat and to the hypervascularization which ensues therefrom. The penetration of the allergen via the pores of the skin is therefore facilitated and the hypervascularization also allows the influx of immunologically competent elements. The reading is carried out after the plastic support has been removed and a sufficient amount of time has been observed, so as to eliminate the non-specific erythema caused by the adhesive material.

In order to allow triggering of the skin reaction, the particles are distributed over the support in an amount which depends on the allergen concerned. As already mentioned, the advantage of the patch is that it provides a device containing a given amount of allergen, entirely delivered, which makes it possible to standardize the patches. For milk for example, the particles are distributed over the support in an amount of between 0.001 and 1 g/cm$^2$.

The invention also relates to a patch kit comprising a plurality of patches as described above, each patch of the kit containing an increasing amount of allergen thus making it possible to increase the allergen doses over the course of the desensitization treatment.

The use of the allergens in the form of particles directly attached to the support, in the dry state, also has the following advantages.

First of all, it makes it possible to avoid any chemical interaction or any reaction which might disturb the allergic process or distort the diagnosis thereof, by bringing only the molecules implicated into contact with the skin. Moreover, the use of the allergen in the form of particles makes it possible to conserve the allergen in a suitable packaging, such that there is no longer any need to carry out an extemporaneous preparation. Finally, the contact of the particles with the sweat exuded by the skin makes it possible to obtain a very concentrated solution promoting rapid penetration of the molecules through the epidermis.

Of course, the patch of the invention is in particular capable of screening the sensitization state with respect to a given allergen, just as with respect to several allergens at once. In the latter case, the support has several areas having electrostatic properties, advantageously in the form of hollows, each covered with a different test allergen, each electrostatic area being separated by a nonelectrostatic area.

According to another embodiment, the patch exhibits, in the same area, a mixture of several allergens for screening the sensitization state of a subject with respect to a series of given allergens. This may be advantageous, for example, for determining the sensitization state of a subject with respect to a series of food allergens. In the case of the combination of several allergens, either arranged on separate electrostatic supports, or mixed on the same support, the choice of the allergens depends on the lists of allergens implicated in the most common pathologies in agreement with the data from the literature. This choice is made so as to form combinations specific for each pathological context in each one of the major age brackets. These lists of allergens are, moreover, able to be modified as a function of the food habits and of the environmental conditions specific to the places where the patches are distributed. In certain cases, the allergens can be chosen from any list published by the health authorities.

The invention also relates to the use of the patch described above, for screening the sensitization state of a subject with respect to an allergen, consisting in applying the patch to the skin, and then, after removing it, in detecting the presence or absence of a skin reaction.

In an advantageous embodiment, the patch is used for screening the sensitization state of a subject with respect to a food allergen contained in the products chosen from the group comprising cow's milk, egg, wheat and peanut.

In another embodiment, the patch is used for screening a subject sensitive to the allergen contained in latex.

The patch of the invention can, moreover, be used for desensitizing a subject to one or more given allergens. In this case, the patch is applied to the skin for a given amount of time depending on the amount of allergen to be delivered. Patches containing increasing amounts of allergens can be used. A programmed release of the allergen from the patch can advantageously be envisioned.

The patch of the invention can be used for the diagnosis of contact allergy, by bringing any contact allergen into contact with the skin, without the addition of gel, blotter or solvent.

It may also be used to administer any biologically active substance for the purpose of obtaining a therapeutic (medicinal product) or preventive (vaccine) or cosmetic action.

The invention and the advantages which ensue therefrom will clearly emerge from the example of implementation which follows in support of the attached figures.

EXAMPLE 1

Figure 1:
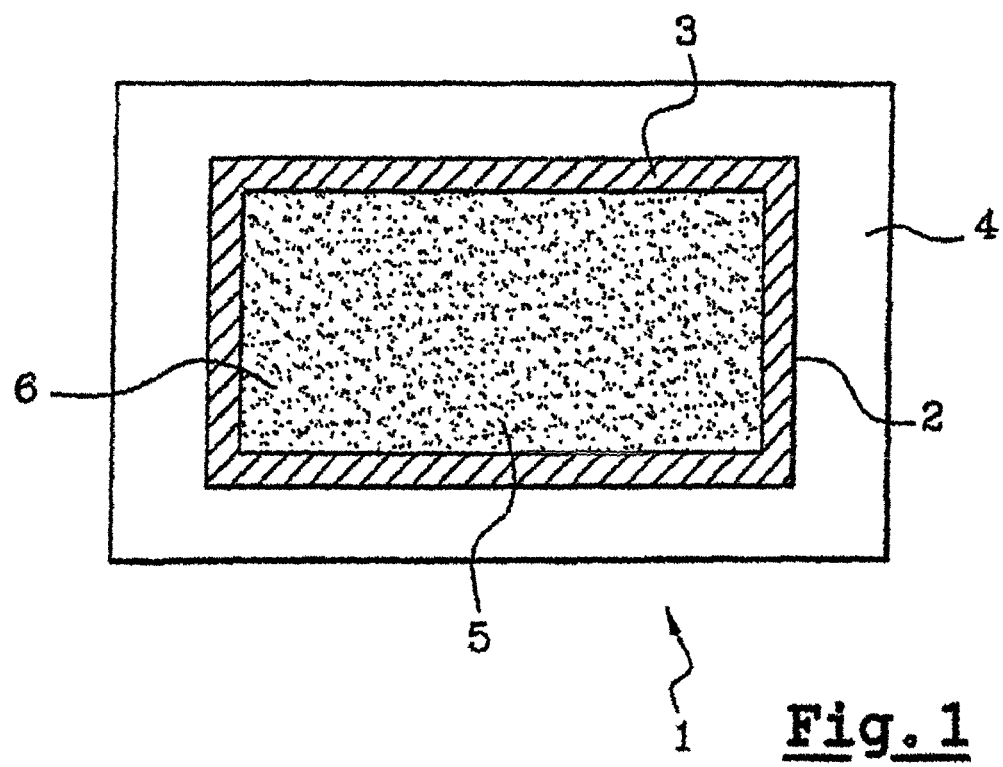
FIG. 1 is a diagrammatic representation of a preferred embodiment of the invention.

FIG. 1 represents the patch of the invention defined by the general reference (1). According to a first characteristic, this patch consists of a support made of cellulose acetate (2), the periphery (3) of which is coated with an adhesive material. The back of the support (2) is also itself covered with a label which can be peeled off (4). As shown in this figure, the allergen (5) is distributed in pulverulent form over the entire non-adhesive area (6) of the acetate support (2).

Figure 2:
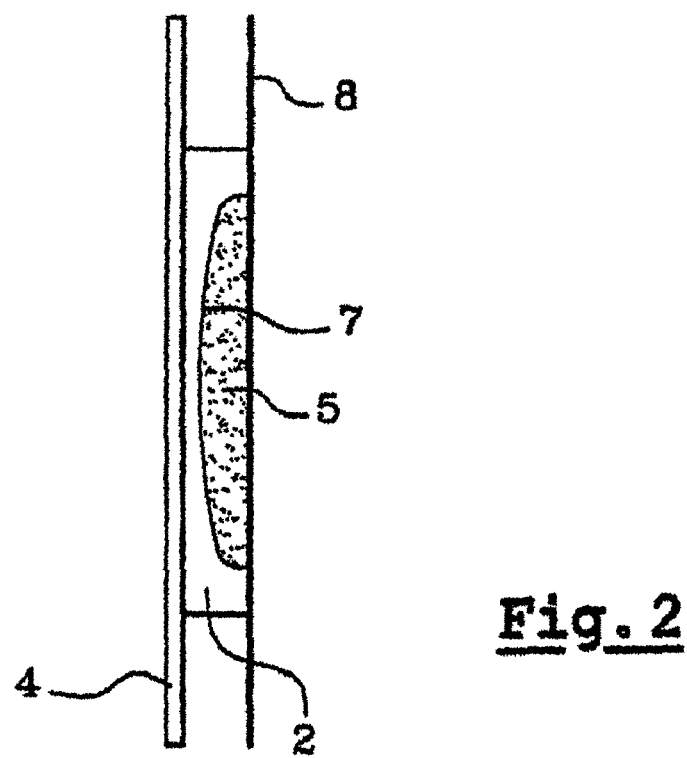
FIG. 2 is a sectional view according to FIG. 1.

As shown in FIG. 2, the acetate support (2) has, over the entire non-adhesive surface,. a depression (7), in which the individualized particles are distributed. The patch has, moreover, a second label which can be peeled off (8), intended to be facing the assembly of acetate support and isolating film-coating (4). This sheet which can be peeled off is, of course, removed before the patch is applied to the area under consideration.

EXAMPLE 2

In this example, the effectiveness of the patches of the invention is compared with patches of the prior art of the FINN CHAMBERS® type.

1—Means and methods

A patch of the invention is applied to the back of 15 children. These children exhibit signs causing an allergy to cow's milk proteins (CMA) to be suspected.

The patch has two areas; a first upper area consisting of an adhesive support onto which is deposited a tablet composed of powdered skimmed milk without any other associated element, which corresponds to the patch of the invention; the lower area consists of the adhesive support onto which is deposited a cupule, the bottom of which is filled with diluted skimmed milk absorbed onto a cellulose support of the FINN CHAMBERS® type.

Reading is carried out 48 hours later, after removal of the adhesive. The presence of erythematous or macular reaction indicates positivity.

2—Results 15 children aged 5 weeks to 11 years and 3/12 were investigated for cow's milk allergy using a double patch. The reaction obtained was evaluated 48 hours after application of the patch.

All the children exhibited clinical signs suggesting a possible allergy to RGO cow's milk proteins, resistant to conventional therapeutic means (9 cases), eczema (6 cases), vomiting (2 cases), chronic abdominal pain (2 cases), chronic diarrhea (3 cases), unexplained manifestations of pain (4 cases), general feeling of being unwell (1 case).

The two tests were positive in 3 cases and negative in 10 cases, the FINN CHAMBERS was positive and the patch negative in one case and, conversely, the FINN CHAMBERS was negative and the patch positive in one case.

3. Conclusion

Among these 15 children suspected of having a food allergy to cow's milk proteins, the patch of the present invention proved to be as sensitive as the FINN CHAMBERS method. In two cases, the results proved to be conflicting, without it being possible to distinguish the two methods.

The invention claimed is:

1. A skin patch comprising:
 a support having an electrically charged surface resulting from the application to the support of an ionizing field;
 an adhesive disposed on the periphery of the support, the adhesive configured to adhere the patch to skin; and
 a preselected amount of an organic allergen, the organic allergen being in the form of individualized or agglomerated dry particles bound to the electrically charged surface through electrostatic forces.

2. The skin patch of claim 1, further comprising a label removably coupled to the adhesive, the label configured to be removed from the adhesive before application of the skin patch to the skin.

3. The skin patch of claim 1, wherein the support comprises glass or a polymer chosen from the group comprising cellulose plastics, polyvinyl chlorides, polypropylenes, polystyrenes, polycarbonates and polyacrylics.

4. The skin patch of claim 1, further comprising a label removably disposed on a back of the support, the label configured to be removed from the skin patch before application to reinforce the electrostatic forces between the organic allergen and the support.

5. The skin patch of claim 1, wherein the organic allergen is a food or respiratory allergen.

6. The skin patch of claim 5, wherein the organic allergen has undergone a treatment of lyophilization, pasteurization or ionization.

7. The skin patch of claim 5, wherein the organic allergen is in the form of a purified allergenic fraction.

8. The skin patch of claim 1, further comprising a marking device in the form of: a marking printed on a back of the support, a temporary tattoo, or a self-adhesive disk maintained on an adhesive part of the support and configured to separate therefrom when the skin patch is removed.

9. The skin patch of claim 5, further comprising a device sensitive to physicochemical reactions of the skin resulting from a local inflammatory reaction.

10. The skin patch of claim 9, wherein the device comprises a colored indicator sensitive to local variations in pH.

11. The skin patch of claim 5, wherein a plurality of different organic allergens are bound to the support.

12. A patch for screening for sensitivity to an allergen, the patch comprising:
a support defining an electrically charged surface resulting from the application to the support of an ionizing field; and
a preselected amount of an organic allergen in the form of individualized or agglomerated dry particles, bound to the electrically charged surface through electrostatic forces, wherein the organic allergen is retained in its reactogenic state.

13. The patch of claim 12, further comprising an adhesive disposed on the support surrounding the electrically charged surface, the adhesive configured to create a hermetically closed space between the support and a patient's skin that contains the organic allergen.

14. The patch of claim 13, wherein the organic allergen is communicated to the patient's skin upon dissolution with perspiration secreted by the patient's skin.

15. The patch of claim 12, wherein the electrically charged surface is disposed within a depression formed in the support.

16. The patch of claim 13 further comprising a label removably coupled to the adhesive, the label configured to be removed from the adhesive before application of the patch to the patient's skin.

17. The patch of claim 12, wherein the support comprises glass or a polymer chosen from the group comprising cellulose plastics, polyvinyl chlorides, polypropylenes, polystyrenes, polycarbonates and polyacrylics.

18. The patch of claim 12, further comprising a label removably disposed on a back of the support, the label configured to be removed from the patch before application to a patient's skin to reinforce the electrostatic forces between the organic allergen and the electrically charged surface.

19. The skin patch of claim 16, wherein the the label, prior to removal, conserves the organic allergen under vacuum.

20. The skin patch of claim 12, wherein the allergen is selected from the group consisting of wheat, peanuts, cow's milk, egg, pollen, acarids, and animal hair.

21. The skin patch of claim 1, wherein the organic allergen is communicated to the skin upon dissolution with perspiration secreted by the skin.

22. The skin patch of claim 1, wherein the support defines a hollow and the organic allergen is bound to the electrically charged surface within the hollow.

23. The skin patch of claim 1, wherein the adhesive is configured to hermetically seal the skin patch to the skin.

24. The skin patch of claim 1, wherein the organic allergen is selected from the group consisting of wheat, peanuts, cow's milk, egg, pollen, acarids, and animal hair.

* * * * *